US00PP07762P

United States Patent [19]

Wilms

[11] Patent Number: Plant 7,762

[45] Date of Patent: Jan. 7, 1992

[54] DAHLIA PLANT NAMED BETTY

[75] Inventor: His J. Wilms, Wognum, Netherlands

[73] Assignee: Royal Sluis, Enkhuizen, Netherlands

[21] Appl. No.: 570,618

[22] Filed: Aug. 21, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner

[57] ABSTRACT

A new and distinct Dahlia plant named Betty, having pure, intense, red-purple flower color, double flower form, dense foliage, continuous flowering, compact flower bouquet carried above the foliage, compact growth habit, and an adaptability to pot plant or natural outdoor cultures.

1 Drawing Sheet

The present invention relates to a new and distinct cultivar of Dahlia plnat known by the cultivar name Betty, and botanically known as *Dahlia cav.*

Betty is a product of breeding and mutation induction programs. The parents were selected plants used in the 1984 breeding program, and are not presently identifiable. The cross was made by the inventor in Enkhuizen, The Netherlands, in 1984. The parents were descendants from the variety Figaro, a well known seed Dahlia, which has created a standard for flower form, habit and leaf size. The breeding line selected out of the progeny of the states cross was designated breeding line number 85207 (deep pink).

Plants from this selected breeding line were subjected to 2,500 rads of gamma radiation, after which cuttings of the irradiated plants were taken. The cuttings were stuck, grown and allowed to flower, and selections made. Selections were based primarily on intensive and unique flower color, early flowering, and large flower diameter, with all of these traits being very significant commercially. Betty was selected and identified by selection No. 86224, and possesses all of these characteristics, especially its beautiful, intense red-purple flower color.

The first act of asexual reproduction of Betty was accomplished when tuberous divisions were taken by the invention from the new cultivar after discovery in a controlled environment in Enkhuizen, The Netherlands. Subsequent horticultural examination of selected units has demonstrated that the combination of characteristics as herein disclosed for Betty are firmly fixed and are retained through successive generations of asexual reproduction. The new cultivar cannot be propagated true to type by seed.

Betty has not been observed under all possible environmental conditions. The phenotype may vary significantly with variations in environment such as temperature, light intensity, and day length. The following observations, measurements and comparisons describe plants grown in Enkhuizen, The Netherlands under greenhouse and outdoor conditions which approximate those generally used in commercial practice.

The following traits have been repeatedly observed and are determined to be basic characteristics of Betty, which in combination distinguish this Dahlia as a new and distinct cultivar:

1. Intense, red-purple ray floret color.
2. Double flower form.
3. Dense foliage.

4. Early flowering.
5. Continuous flowering, with the flowers being carried above the foliage.
6. Compact growth habit.
7. Adaptable to pot plant culture as well as natural outdoor growth.

Relevant cultivars for comparison purposes are the seed varieties Rigoletto and Figaro. In comparison to Rigoletto, Betty is more compact, has a double flower form, and a purer red-purple ray floret color. Betty is distinguished from Figaro by its more compact habit, earlier flowering, and the purity of its ray floret color. The term "purity" refers to a uniform color without tingeing or overlay. Betty can also be compared to the tuberous propagated cultivar Carol, disclosed in U.S. Plant Pat. No. 6,926. Both cultivars have dense foliage, continuous flowering, compact habit, and red-purple floret color. Betty can be distinguished from Carol by Betty's much darker red-purple ray floret color. Also, Betty is a more double-flowered variety, and its leaves are smaller and a darker green.

The accompanying color photographic drawing is a perspective view showing typical inflorescence and foliage characteristics of Betty, with colors being as nearly true as possible with illustrations of this type. In the following description color references are made to The Royal Horticultural Society Colour Chart. The color values were determined at Enkhuizen, The Netherlands, and the characteristics noted below are based on plants grown at the same location.

Classification:

*Botanical.*—*Dahlia cav.* cv Betty (Group IV, peony flowered, classification of International Dahlia Register, 1969).

*Commercial.*—Dahlia.

Parentage:

A selection from an induced irradiation program involving gamma irradiation of plants of the selected breeding line 85207 (deep pink), which resulted from a cross of unknown parents.

Plant:

*Form.*—Generally round.

*Size.*—Approximately 19 cm in height (from top of pot) at time of flowering.

*Growth habit.*—Compact.

*Foliage.*—Size: Length small, approximately 5.5 cm; width approximately 3.5 cm. Quantity: Abundant, dense. Color: Dark green, approximately 137A. Shape: Narrow, generally ovate, edges serrated, tip acute. Texture: Relatively dull.

Flowers:

*Form.*—Double.

*Shape.*—Overall inflorescence is generally flat, with petals being generally blunt but having slightly pointed tips; firm.

*Size.*—Individual ray florets approximately 3.5 cm long and 2.0 cm wide; overall inflorescence approximately 7–8 cm in diameter.

*Borne.*—On pedicels which are approximately 6 cm in length (from flower to top part of leaves); top of the pedicel oriented at approximately 120° to the vertical axis of the plant; flowers carried compactly above the foliage; very floriferous.

*Continuity.*—Continuously flowers outdoors after first flower opens.

*Stems.*—Color of new stem is green, with flowering stem having red-green coloration.

*Color.*—Fully open: Upper surface 66B. Under surface 66D. Half open: Upper surface 66A. Under surface 66C.

Reproductive organs: Normal.

I claim:

1. A new and distinct cultivar of Dahlia plant named Betty, as illustrated and described.

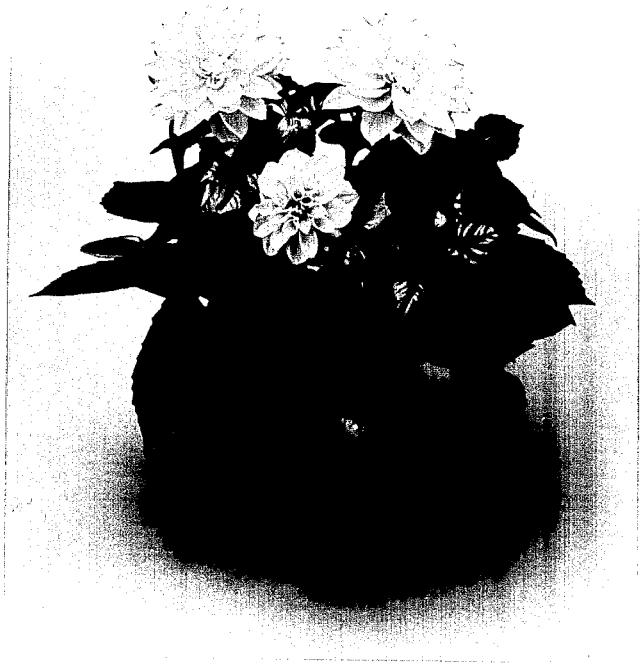

* * * * *